United States Patent [19]

Brusilow

[11] Patent Number: 4,457,942
[45] Date of Patent: Jul. 3, 1984

[54] PROCESS FOR WASTE NITROGEN REMOVAL

[76] Inventor: Saul W. Brusilow, Dept. of Pediatrics, The Johns Hopkins Hospital, Baltimore, Md. 21205

[21] Appl. No.: 410,018

[22] Filed: Aug. 20, 1982

[51] Int. Cl.³ ............................................. A61K 31/19
[52] U.S. Cl. ................................................... 424/317
[58] Field of Search ......................................... 424/317

[56] References Cited

U.S. PATENT DOCUMENTS 4,284,647  8/1981  Brusilow et al. ..................... 424/317

OTHER PUBLICATIONS

Principles of Biochemistry, pp. 439-440, White et al., 3rd ed., McGraw-Hill.
Kariev, Chem. Abst., 95:163755a, 1981.

Primary Examiner—Stanley J. Friedman
Assistant Examiner—John W. Rollins
Attorney, Agent, or Firm—Murray, Whisenhunt and Ferguson

[57] ABSTRACT

A method of alleviating the accumulation of waste nitrogen in human beings is disclosed, wherein phenylbutyrate, or even numbered conger thereof, is administered to a patient having such waste nitrogen accumulation. The phenylbutyrate or other compound is broken down by beta-oxidation to eventually yield phenylacetate, which is known to be useful for removing waste nitrogen from the blood stream.

The present invention provides a solution to the offensive odor of phenylacetate, which is unpalatable to patients, and also can eliminate peaks and valleys of drug levels in the patient, due to the gradual formation of the desired compound phenylacetate in the patient's body.

10 Claims, No Drawings

PROCESS FOR WASTE NITROGEN REMOVAL

BACKGROUND OF THE INVENTION

The present invention relates to a method of alleviating the accumulation of waste nitrogen in human beings.

In a healthy person, the potentially toxic nitrogenous compounds which accumulate as the body degrades proteins are synthesized into urea which is rapidly excreted into the urine. However, for those who suffer kidney failure, liver failure or inborn errors of urea synthesis this pathway is defective. The accumulation of nitrogenous compounds resulting from such a blockage leads to considerable morbidity and mortality.

In the case of an inborn error of urea synthesis, the major metabolic abnormality is the inability of the body to convert waste nitrogen into urea. As a consequence, various nitrogenous metabolites accumulate in the body, the most toxic being ammonium although other materials, such as glutamine, glutamate and alanine, also increase.

Previous therapeutic approaches for treating patients with urea cycle enzymopathies (as well as other nitrogen accumulation diseases cited earlier) have been designed to reduce the requirement for urea synthesis by quantitative and qualitative manipulation of dietary protein, amino acids and/or their nitrogen free analogues. Generally speaking, however, the mortality of inborn errors of the urea-cycle remained high and success was measured in terms of increased survival time. Thus, for example, even with the above-cited therapeutic approaches children with the neonatal form of these diseases rarely survived past one year of age.

A more recent approach to remedy this pervasive problem is described in U.S. Pat. No. 4,284,647 where benzoic acid, phenylacetic acid, or the salts thereof convert the waste nitrogen into amino acid acylation products which the body can successfully excrete as urinary nitrogen. More specifically, that patent teaches that phenylacetate reacts with the nitrogen to form phenylacetylglutamine which is subsequently excreted by the body. Since such a reaction is in no way dependent on the urea synthesis or excretion, it is an effective treatment from those suffering from nitrogen accumulation diseases. See also "Treatment of Inborn Errors of Urea Synthesis," *New England Journal of Medicine*, 306; 1387–1392 (1982).

It is well known that there is considerable species specificity in the amino acid that conjugates with phenylacetate. (James M. D., Smith, R. L., Williams, R. T., and Reidenberg, M., "The Conjugation of Phenylacetic Acid in Man, Sub-human Primates and Some Nonprimate Species," Proc. R. Soc. Lond. B. 182: 25–35, 1972; Power, F. S., Detoxification of Phenylacetic Acid by the Chimpanzee. Proc. Soc. Exptl. Biol. Med 33: 598, 1935). Only man, the baboon and the chimpanzee completely or nearly completely conjugate phenylacetate with glutamine whereas other species conjugate it with glycine (as in the dog), taurine, ornithine or glucuronic acid.

Despite the effectiveness of the phenylacetate treatment, specific drawbacks have been encountered in its use. The compound, which is generally administered to patients orally, has a vile and pervasive odor which renders it virtually unpalatable. Thus, patients fail to comply with the prescribed treatment due to their reluctance to subject themmselves to this odor, and this reluctance can be a serious problem in successful therapy. Another disadvantage of the phenylacetate results from the division of the daily dosage. After administering the compound, the waste nitrogen present in the patient quickly reacts to form the amino acid acylation product and plasma levels of phenylacetate fall to nearly zero in six hours. At this point no further amino acid acetylation can occur unless another dose of phenylacetate is given.

Phenylbutyrate in all mammals including man is metabolized to phenylacetate by the fatty acid beta-oxidation mechanism because the side chain is even numbered. (Lehninger, A., Biochemistry, Worth Publishers, N.Y., (1976.)

BRIEF SUMMARY

The present invention overcomes the above-identified disadvantages of phenylacetate by substituting for the phenylacetate compounds of the general formula:

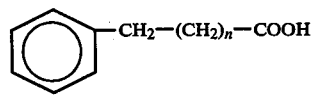

where n is 2, 4, 6, or 8.

When administered to humans even numbered phenylalkanoic acids, such as phenylbutyrate, can be broken down by beta-oxidation, two carbon atoms at a time, to eventually yield phenylacetate which, as described above, has been found useful for removing waste nitrogen from the blood stream. Unlike phenylacetate, however, these higher molecular weight compounds do not have the offensive odor which renders phenylacetate so unpalatable. Thus, with the unpleasant odor eliminated, a patient is much less likely to deviate from his prescribed treatment. The substitution of phenylacetate by the compounds of the present invention can also eliminate the peaks and valleys in drug levels since the breakdown of these higher molecular weight compounds by beta-oxidation is a gradual process.

DESCRIPTION OF THE INVENTION

The present invention utilizes compounds of the formula

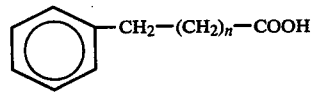

where n equals 2, 4, 6 or 8 and where the compound is either in the acid form as shown or a pharmaceutically acceptable salt thereof.

The compounds of the present invention can be used separately or in the form of mixtures, including mixtures of acids and/or salts. The amount of the compounds of the present invention, whether in the form of the acid and/or the salt thereof, which are administered to patients for the present purposes can vary widely from case to case. Normally, however, the daily dosage for the compounds should fall in the range of 100 to 400 mg/kg body weight for children, and from 7.5 to 15 grams for adults. The size and frequency of the dosages given at any time may be varied as desired provided the indicated total daily dose is not significantly modified. The administration may be carried out intravenously or orally (e.g. in the form of sterile injectable solutions, pills, tablets, capsules, solutions, suspensions or the like).

In their experiments with dogs, Raper and Wagner (Biochem Journal 22:188 (1928)) demonstrated that compounds of the above formula are oxidized at the beta carbon during metabolism to cause cleavage of two carbons at a time. Thus, they found that 80% of the phenylbutyrate administered to dogs appeared in the urine as the glycine conjugate of phenylacetate. Unlike dogs, man only produces an acetylation product of glutamine from phenylacetate. Thus, when phenylbutyrate is administered to a human as either a fatty acid or a salt thereof, the phenylacetate formed as a result of beta oxidation will acetylate the glutamine thus causing the formation of phenylacetylglutamine which will be excreted by the kidney. The beta oxidation process is not limited to phenylbutyrate. In fact, any even numbered phenylalkanate can be metabolized to phenylacetate. Thus phenylhexanoate, phenyloctanoate and phenyldecanoate are also effective to control waste nitrogen levels. Like phenylbutyrate, these compounds do not have the strong disagreeable odor characteristic of phenylacetate. In fact, sodium phenylbutyrate is virtually odorless when compared to sodium phenylacetate. The use of phenylbutyrate, such as in the form of the sodium or calcium salt, is preferred.

It is anticipated that the toxicity of phenylbutyrate and other compounds of this invention to patients would be low when these compounds are administered to patients because the principal, if only, fate of such compounds is beta oxidation to form phenylacetate. The phenylacetate metabolic product, on the other hand, has no known toxicity and is approved for investigational use in humans (IND #17123).

The method of treating disorders involving nitrogenous waste accumulation is more fully set forth in U.S. Pat. No. 4,284,647, the disclosure of which is hereby incorporated by reference for the teachings of such method.

What is claimed is:

1. A process for controlling waste nitrogen accumulation disease in a patient suffering from such waste nitrogen accumulation disease caused by an impairment in the normal synthesis of urea from ordinary waste nitrogen in the body or in the normal excretion thereof, said process comprising administering to the patient an effective amount of at least one compound of the formula:

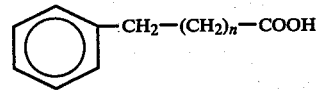

wherein n is 2, 4, 6 or 8, or a pharmaceutically, acceptable salt thereof, and wherein the amount of said compound administered to the patient is sufficient to produce enough phenylacetate to react with waste nitrogen to form an amino acylation product for urinary discharge of said product.

2. The process of claim 1 wherein the administration is continued until the accumulated waste nitrogen is discharged as urinary nitrogen.

3. The process of claim 1 wherein the patient is one with a urea cycle enzymopathy.

4. The process of claim 1 wherein the patient is one suffering from renal failure.

5. The process of claim 1 wherein the patient is one suffering from a hepatic failure.

6. The process of claim 1 wherein said compound is phenylbutyrate, or a salt thereof.

7. The process of claim 1 wherein the salt is the calcium salt.

8. The process of claim 1 wherein the salt is the sodium salt.

9. The process of claim 1 wherein the compound is orally administered.

10. The process of claim 1 wherein the compound is administered intravenously.

* * * * *

UNITED STATES PATENT AND TRADEMARK OFFICE

CERTIFICATE EXTENDING PATENT TERM
UNDER 35 U.S.C. § 156

PATENT NO.      :   4,457,942

ISSUED          :   July 3, 1984

INVENTOR(S)     :   Saul W. Brusilow

PATENT OWNER    :   Ucyclyd Pharma, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Two years from August 20, 2002, the original expiration date of the patent, with all rights pertaining thereto as provided by 35 U.S.C. § 156(b).

I have caused the seal of the Patent and Trademark Office to be affixed this 20th day of November 1997.

Bruce A. Lehman
Assistant Secretary of Commerce and
Commissioner of Patents and Trademarks